(12) United States Patent
Mao et al.

(10) Patent No.: US 10,130,258 B2
(45) Date of Patent: Nov. 20, 2018

(54) ASSISTIVE SAMPLE COLLECTION AND STORAGE ASSEMBLY

(71) Applicant: General Electric Company, Schenectady, NY (US)

(72) Inventors: Ying Mao, Niskayuna, NY (US); Weston Blaine Griffin, Niskayuna, NY (US); Erin Jean Finehout, Clifton Park, NY (US); Ian Hart, Nassau, NY (US)

(73) Assignee: General Electric Company, Schenectady, NY (US)

( * ) Notice: Subject to any disclaimer, the term of this patent is extended or adjusted under 35 U.S.C. 154(b) by 1458 days.

(21) Appl. No.: 14/035,085

(22) Filed: Sep. 24, 2013

(65) Prior Publication Data

US 2018/0299354 A1    Oct. 18, 2018

(51) Int. Cl.
*A61B 5/00*    (2006.01)

(52) U.S. Cl.
CPC .................. *A61B 5/0051* (2013.01)

(58) Field of Classification Search
CPC ............ A61B 10/0045; A61B 10/0051; A61B 10/0096
USPC .......................................................... 600/572
See application file for complete search history.

(56) References Cited

U.S. PATENT DOCUMENTS

| | | |
|---|---|---|
| 5,169,789 A | 12/1992 | Bernstein |
| 6,010,462 A | 1/2000 | Stoermer, III |
| 6,291,171 B1 | 9/2001 | Ricciardi et al. |
| 7,670,849 B2 | 3/2010 | Henkin |
| 7,748,283 B2 | 7/2010 | Harvey et al. |
| 7,749,775 B2 | 7/2010 | Maher et al. |

(Continued)

FOREIGN PATENT DOCUMENTS

| | | |
|---|---|---|
| GB | 2491807 A | 12/2012 |
| WO | 9008817 A1 | 8/1990 |
| WO | 2013064558 A1 | 5/2013 |

OTHER PUBLICATIONS

PCT Search Report and Written Opinion issued in connection with corresponding PCT Application No. PCT/EP2014/070407 dated Dec. 18, 2014.

(Continued)

*Primary Examiner* — Max Hindenburg
(74) *Attorney, Agent, or Firm* — GE Global Patent Operation; Seema Katragadda

(57) ABSTRACT

An assistive sample collection and storage assembly for collecting, transferring and storing a biological sample includes a sample collection device having a first portion and a second portion. The first portion is configured to receive a sample collection member. The assembly includes a sample storage device comprising a sample substrate configured to receive at least a portion of the biological sample from the sample collection member. The assembly is configured to exist in a first state and a second state. The sample collection member is disposed at a determined distance from the sample substrate in the first state. At least a portion of the sample collection member is in physical contact with at least a portion of the sample substrate in the second state. The sample collection member is configured to apply a determined amount of contact force between the collection member and the sample substrate in the second state of the assembly.

16 Claims, 9 Drawing Sheets

(56) References Cited

U.S. PATENT DOCUMENTS

| | | |
|---|---|---|
| 8,278,091 B2 | 10/2012 | Rutter et al. |
| 8,293,489 B2 | 10/2012 | Henkin |
| 8,355,132 B2 | 1/2013 | Xia et al. |
| 9,534,990 B2 * | 1/2017 | Smith ................... B01L 7/00 |
| 2004/0116826 A1 | 6/2004 | Jung et al. |
| 2012/0135444 A1 | 5/2012 | Bernatchez et al. |

OTHER PUBLICATIONS

PCT Search Report and Written Opinion issued in connection with corresponding PCT Application No. PCT/EP2014/070407 dated Feb. 13, 2015.

* cited by examiner

ASSISTIVE SAMPLE COLLECTION AND STORAGE ASSEMBLY

This invention was made with Government support under grant number HR0011-11-C-0127 awarded by the Defense Advanced Research Projects Agency (DARPA). The Government has certain rights in the invention.

BACKGROUND

The invention relates to collection and storage of biological samples, and more particularly to devices configured to collect, transfer and store the biological samples.

The collection of biological samples (such as blood) and extracting DNA for genetic analysis from the sample have been widely used by the forensics and medical community for identification purposes such as, but not limited to, paternity testing, genetic diagnostic testing in new born screening programs, genetic typing for predisposition to a particular disease, and genetic characterization for drug susceptibility. Typically, collected biological samples are stored in a dried state on an absorbant material. By way of example, dried blood spots are commonly stored on substrates.

Typically, for sample storage of the biological samples, it is desirable to use substrates that facilitate efficient and reproducible transfer of the collected samples to a substrate card. However, typically, the success of the transfer of the collected samples depends on skills of the user. Accordingly, the sample transfer process is adversely affected in point-of-care type settings where the person (e.g., a nurse, or a patient) collecting the sample may have inadequate training in the sample collection and transfer. Moreover, when compared to other samples, such as substrate based samples, the sample transfer success rate is relatively lower for swabbed samples (such as a buccal swab, nasal swab, or swab of a wound area) as the user needs to apply the sample to the correct location for sample collection and use the right amount of force to transfer the sample from the swab to the sample substrate. For example, if less than a desirable force is applied to transfer the sample from the swab to the sample substrate, the sample may not be efficiently transferred to the sample substrate. On the other hand, if the force applied to the swab is more than the desirable force, the storage substrate may suffer damages.

BRIEF DESCRIPTION

In one embodiment, an assistive sample collection and storage assembly for collecting, transferring and storing a biological sample is provided. The assembly includes a sample collection device and a sample storage device. The sample collection device includes a first portion and a second portion, where the first portion of the sample collection device is configured to receive a sample collection member, wherein the second portion is connected to the first portion by a rotating element. Further, the sample collection device is configured to rotate the sample collection member about a longitudinal axis of the sample collection member. The sample storage device includes a sample substrate configured to receive at least a portion of the biological sample from the sample collection member. The assembly is configured to exist in a first state and a second state. In the first state of the assembly, the sample collection member is disposed at a determined distance from the sample substrate. Whereas, in the second state, at least a portion of the sample collection member is in physical contact with at least a portion of the sample substrate. Moreover, in the second state, the sample collection member is configured to apply a determined amount of contact force between the sample collection member and the sample substrate.

In another embodiment, an assistive sample collection and storage assembly for collecting, transferring and storing a biological sample is provided. The assembly includes a sample collection device and a sample storage device. The sample collection device includes a first portion and a second portion. The first portion of the sample collection device includes a sample collection member having a handle. The second portion of the sample collection device is configured to be coupled to the first portion and the sample storage device.

In yet another embodiment, a method for collecting, transferring and storing a biological sample using an assistive sample collection and storage assembly is provided. The method includes providing a sample collection member, collecting the sample using the sample collection member. Further, the method includes providing a sample storage device having a sample substrate, and providing the assistive sample collection and storage assembly comprising the sample collection device and the sample storage device. Moreover, the method includes switching a state of the assistive sample collection and storage assembly such that at least a portion of the sample collection member is in physical contact with at least a portion of the sample substrate, where the sample collection member is in physical contact with the sample substrate at a determined angle. Moreover, the method includes rotating the sample collection member to facilitate transfer of at least a portion of the sample from the sample collection member to the sample substrate.

DRAWINGS

These and other elements and aspects of embodiments of the present disclosure will become better understood when the following detailed description is read with reference to the accompanying drawings in which like characters represent like parts throughout the drawings, wherein.

Figure 10A:
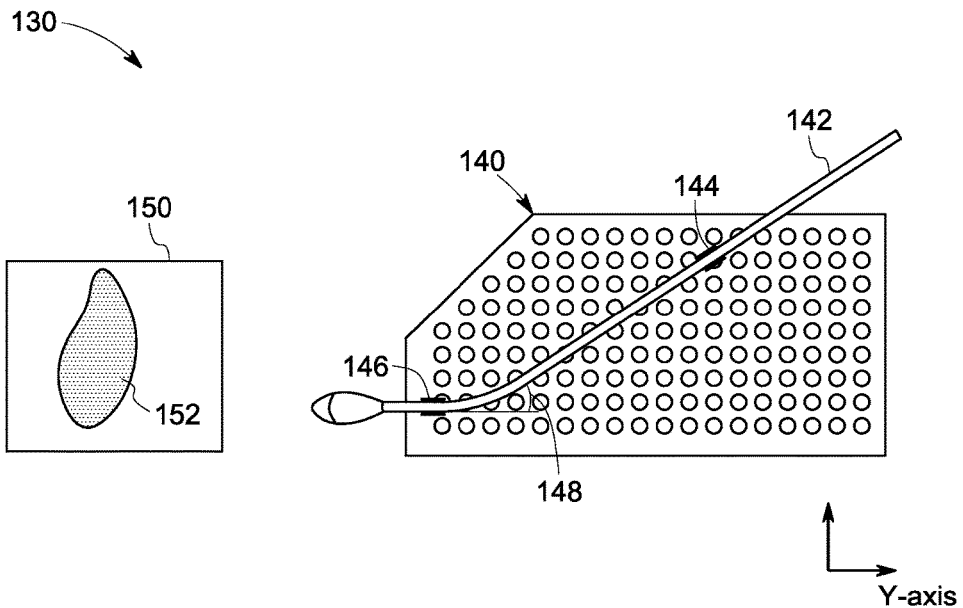
Figure 10B:
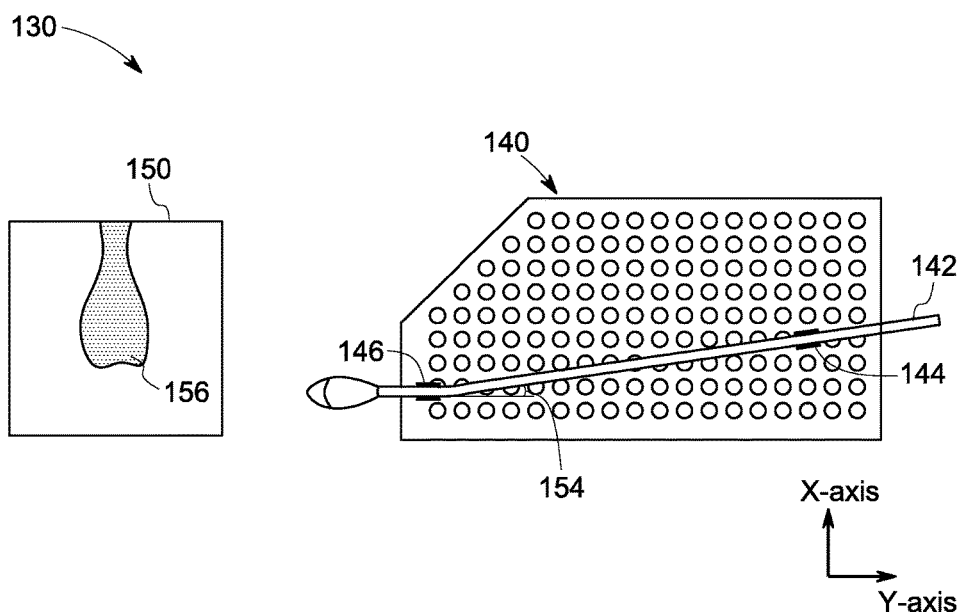
Figure 11:
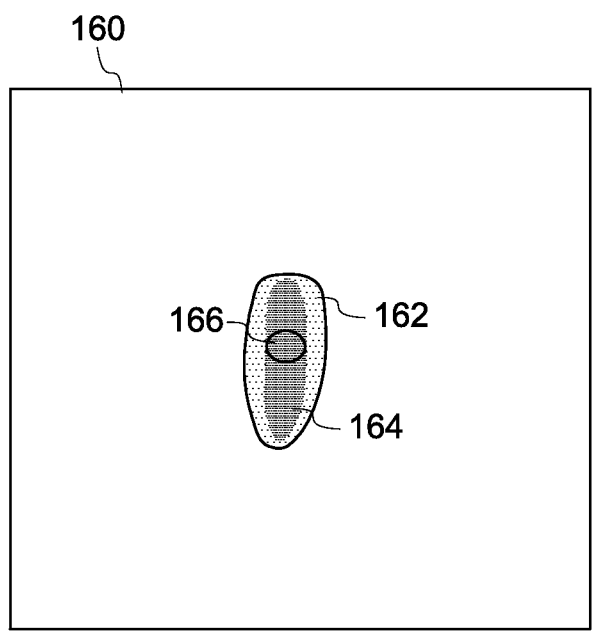

FIGS. 10(*a*)-10(*b*) are cross-sectional views of an experimental set-up configured to assess an effect of a bending angle of a swab on a location and amount of sample transferred on a sample substrate, in accordance with aspects of the present disclosure; and FIG. 11 is a schematic representation of overlapping images of a sample transferred from a swab to a sample substrate.

DETAILED DESCRIPTION

Embodiments relate to assistive sample collection assemblies configured to assist in collection, transfer and storage of a biological sample in a controlled manner. By way of example, the assistive sample collection assemblies are configured to transfer the biological sample to a desirable location on a sample substrate in a reproducible manner. It should be noted that the terms "sample" and "biological sample" may be used interchangeably throughout the application. In certain embodiments, the assistive sample collection and storage assembly may be used to collect degradable biologically sourced analytes such as nucleic acids, proteins, and respective fragments thereof. Non-limiting examples of the biological sample may include saliva, blood, serum, lymph fluids, buccal cells, mucosal cells, cerebrospinal fluid, semen, feces, plasma, urine, a suspension of cells, or a suspension of cells and viruses. In addition, the biological samples may include samples from flora and fauna. In a non-limiting example, the biological samples may include plant or fungal samples for the study of population genetics. Also, in one example, the assembly may be used for collection of the biological samples for purposes, such as, but not limited to, collection of buccal cell samples for criminal databases, collection of crime scene samples (i.e., rehydrated blood, semen, saliva and liquid samples of the same); collection of sexual assault samples; collection of buccal samples for population genetics or pharmacogenomics studies; collection of nasal samples for respiratory infection diagnosis; collection of bacterial or parasite samples from food sources; collection of blood from meat at a slaughterhouse for meat traceability; or collection of biological samples from animals for veterinary diagnostics. It should be noted that at the time of collection, the biological samples may or may not exist in a biological body from where the sample originated. By way of example, the biological sample may include a blood sample splattered on a floor of a crime scene.

In certain embodiments, the assistive sample collection and storage assembly may include a sample collection device and a sample storage device. As used herein, the terms "assistive sample collection and storage assembly," "assistive assembly," and "assembly" may be used interchangeably. The sample collection device is configured to receive at least one sample collection member. The sample collection member is configured to collect a biological sample. In some embodiments, the sample collection member may include an analyte collection surface. The analyte collection surface may include an analyte collection medium. In certain embodiments, the sample collection member may be disposed outside the sample collection device while collecting the sample. In these embodiments, the sample collection member is coupled to the sample collection device after collecting the sample. In certain other embodiments, the sample collection member may be disposed, at least in part, in the sample collection device while collecting the sample. The sample storage device includes a sample substrate. The sample substrate may be configured to receive and store the sample from the sample collection member.

For analysis of the biological sample, the sample collection device and the sample storage device are operated so as to transfer at least a portion of the sample from the sample collection member to the sample storage device. By way of example, the sample collection device containing a sample collection member is coupled to a sample storage device such that a portion of the sample collection member having the sample is brought in physical contact with a portion of the sample storage device to facilitate the transfer of the sample from the sample collection member to the sample storage device.

In one embodiment, the sample collection device may be releasably coupled to the sample storage device. By way of example, the sample collection device may be releasably coupled to the sample storage device at least during transfer of at least a portion of the sample from the sample collection member to the sample storage device. In one example, the sample substrate may be configured to receive the sample from the sample collection member upon physical contact between the sample collection member of the sample collection device and the sample substrate of the sample storage device. The portion of the sample transferred from the sample collection member to the sample storage device may be stored on the sample substrate. In certain embodiments, the sample storage device may include a storage medium suitable for collecting and storing the biological sample. The storage medium may be disposed on a surface of the sample substrate of the sample storage device. In some embodiments, a surface of the sample substrate may be a volume of a foam pad, for example, and not just a contact surface area of the sample substrate. As used herein, the phrase "store the sample" or "storing the sample" may encompass the steps of disposing the sample on the sample substrate and drying the sample.

One or more parts of the assistive sample collection and storage assembly may be configured for one time use to reduce or prevent contamination or spreading of infection via the sample collection and storage assembly. In one example, the sample collection device may be a disposable device. In some embodiments, the design of the assistive sample collection and storage assembly facilitates collection, transfer and storage of the sample, while preventing any undesirable contact of the user with the sample while transferring the sample from the sample collection member to the sample storage device, or while storing the sample. Advantageously, in some embodiments, the assistive sample collection and storage assembly may be configured to receive off-the shelf sample collection members, such as, but not limited to, swabs, for collection of the biological samples. Furthermore, the assembly may be used by any person, including a patient, and may not necessarily need a technician or skilled operator to collect, transfer or store the sample. In certain embodiments, the assistive sample collection and storage assembly may be configured for consistent and reproducible collection, transfer and storage of biological samples. In certain embodiments, a percentage of the biological sample transferred from the sample collection member to the sample storage device may be reproducible. In certain embodiments, the position of biological sample on the sample substrate transferred from the sample collection member to the sample storage device is reproducible.

In certain embodiments, for analysis of the biological sample after collection, a suitable storage medium may be selected so as to remove at least a portion of a biologically sourced analyte present on the storage medium. Non-limiting examples of suitable storage media may include cellulose, such as #903® brand paper (GE Healthcare) or chemically impregnated celluloses, such as FTA® and FTA® Elute brand paper (also from GE Healthcare). These storage media provide a simple method for collection, shipping and storage of biological samples. These storage media also contain chemistries which facilitate easy isolation of DNA from complex samples such as blood. Samples collected on treated or untreated storage media are dried for storage and can be stored at room temperature for long periods of time.

Moreover, in some embodiments, the storage media may include at least one stabilizing reagent that preserves at least one biological sample analyte for transport or storage. Non-limiting examples of suitable reagents for the storage media may include one or more of a weak base, a chelating agent, and, optionally, uric acid or a urate salt or simply the addition of a chaotropic salt, alone or in combination with a surfactant. In one embodiment, the storage media may have a visual delineation disposed around the transfer area of the storage medium such that, if the sample storage device is removed from the sample collection device, an operator may know where the material was deposited without reference to the device.

Furthermore, in certain embodiments, the assistive sample collection and storage assembly may use a dry solid storage and transfer medium and a method for the collection of biological material of interest (genetic or proteinaceous material) in a form suitable for storage and/or subsequent analysis. The analyte collection surface may include an analyte collection medium suitable for collecting the sample.

In one embodiment, the sample collection member may be pre-fitted in the sample collection device. By way of example, the sample collection member may be a factory fit in the sample collection device. In an alternative embodiment, the sample collection member may be available separately, and may be coupled to the sample collection device as required. Also, In one embodiment, the sample collection member may be used to collect the sample prior to being coupled to the sample collection device. In another embodiment, the sample collection member may be coupled to the sample collection device before collecting the sample. Non-limiting examples of the sample collection member may include a flocked swab, cotton-tipped applicator, foam-tipped applicator, or combinations thereof. In one example, the sample collection member may include an off-the-shelf swab. In another example, the swab may be a customized swab that is designed to suit requirements (e.g., size, shape) of the user and the sample collection device. Non-limiting examples of the swab designs may include cylindrical swabs that are symmetric about their longitudinal axis. However, other kinds of swabs, such as, but not limited to, non-symmetrical swabs (e.g., cone shaped swabs) may also be used.

Further, the sample collection device may include elements to dispose the sample collection member such that when the sample collection member comes in physical contact with the surface of the sample substrate, also referred to as "substrate surface". The contact is at a desirable angle to facilitate transfer of the sample to the substrate surface. In addition, the sample collection device may be configured to provide reproducible contact force between the sample collection member (e.g., swab) and the sample substrate. Further, the sample collection device may be configured to provide a reproducible transfer location for the sample on the sample substrate. Moreover, the sample collection device may be configured to provide determined amount of collected sample volume as well as sample concentration (sample volume per unit area of the sample substrate) that is compatible with downstream sample elution and analysis. Furthermore, the sample collection device provides an ergonomically suitable design to enable trained as well as untrained users to operate the device in a non-clinical setting. Advantageously, the sample collection device provides elements that facilitate storage of the sample while preventing user contact with the sample, or user contact with the sample substrate to prevent the user from coming in contact with any hazardous chemicals or materials that are not bio-compatible.

In some embodiments, the sample collection device may include provisions to be releasably coupled to the sample storage device. Thus, one can separate the sample storage device from the collection device for subsequent processing or storage. In one embodiment, a coupling element between the sample collection device and the sample storage device may be configured to allow for manual or automated release of the sample storage device, but not allow for accidental loss of the sample storage device from the assembly.

In some embodiments, the assistive sample collection and storage assembly may have a monolithic structure. In some of these embodiments, the sample collection device and the sample storage device may form an integrated structure. In some other embodiments, the assistive sample collection and storage assembly may include two or more physically independent portions. By way of example, the physically independent portions of the assembly may include a sample collection device and a sample storage device. The sample collection device and sample storage device may be releasably or permanently coupled to one another to form the assistive sample collection and storage assembly.

Further, in some embodiments, the sample collection device may have a monolithic structure. In some other embodiments, the sample collection device may include two or more portions. In one embodiment, the two or more portions of the sample collection device may be operatively coupled via a coupling element. In one such embodiment, the coupling element may be a flexure between the two or more portions of the sample collection device. In one example, a first portion of the sample collection device may be releasably coupled to the second portion of the sample storage device. In another example, the first portion of the sample collection device may be releasably coupled to the sample collection member. Non-limiting examples of the coupling element may include fasteners, such as, but not limited to, slots and pins.

The sample collection device may include provisions for a bi-state design of the assistive sample collection and storage assembly. In a first state of the assembly, the sample collection member may be disposed away from the sample substrate. More particularly, in the first state of the assembly, the portion of the sample collection device having the sample collection member and the other portion of the sample storage device are locked such that the sample collection member is disposed away from the sample substrate. In a second state of the assembly, the portion of the sample collection device having the sample collection member and the other portion of the sample storage device are locked such that at least a portion of the sample collection member is in physical contact with at least a portion of the sample substrate.

In certain embodiments, the sample collection device may include a receiver that is configured to receive the sample collection member. The receiver may be a snap-in element, a clip element, an adhesive based element, or any other design that is able to receive the sample collection member (e.g., an off-the-shelf swab). The sample collection member may be permanently or releasably coupled to the receiver.

Additionally, in certain embodiments, an analyte collection surface of the sample collection member may include surfaces, such as, but not limited to, a flocked surface. The analyte collection surface may be dimensioned and configured such that the volume of the sample being transferred from the sample collection member to the sample substrate is controlled. By controlling the volume of the transferred sample, overloading of any stabilizing reagents disposed on the storage medium with respect to the respective protecting capacity of the stabilizing reagents may be reduced or prevented. If used in nasal swab applications, the analyte collection surface may be dimensioned and configured to fit within the human nasal cavity. Accordingly, when used in buccal swab applications, the analyte collection surface should be dimensioned and configured to fit within the human mouth.

In some embodiments, for record keeping and traceability, the present device may also include an identification label (such as conventional bar coding). In one example, the identification label may be disposed on the sample collection device and the sample storage device.

To ensure device integrity, in some embodiments, the assistive sample collection and storage assembly may include a sterility envelope surrounding device elements or devices of the assistive sample collection and storage assembly. In some embodiments, the elements or devices of the assistive sample collection and storage assembly may be made from medical grade plastics. Additionally, the elements or devices of the assistive sample collection and storage assembly may be free from contaminates and leachable materials (e.g., USP Class VI materials). Moreover, the elements or devices of the assistive sample collection and storage assembly may be sterilized through conventional techniques such as irradiation after the envelope is sealed. Kits may be made that incorporate the above device along with any combination of associated equipment or reagents including purification reagents, buffers, or the like and storage systems, containers, or the like.

In one example embodiment, the assistive sample collection and storage assembly may include a sample collection member-bending approach. In this sample collection member-bending approach, a natural stiffness/flexibility of a body of sample collection member may be used to press a head of the sample collection member against the sample substrate to produce proper contact force and facilitate transfer of a desirable portion of the sample from the sample collection member to the sample substrate. In some embodiments, the user may rotate the sample collection member (e.g., a swab) one or more times to facilitate physical contact between the head of the sample collection member and the sample substrate.

Advantageously, systems and methods described herein are configured to provide and address one or more issues associated with reliable collection, transfer, and storage of the biological sample on the sample substrate: 1) reproducible contact force between the sample collection member and the sample substrate 2) reproducible transferred sample location on the sample substrate, percentage of transferred volume and sample concentration (volume per unit area) to be compatible with downstream sample elution and analysis; 3) ergonomically suitable to allow a wider range of users including untrained users in the field, or non-clinical settings. 4) safe for the user to prevent undesirable user contact with the sample substrate that may contain hazardous chemicals.

Figure 1:
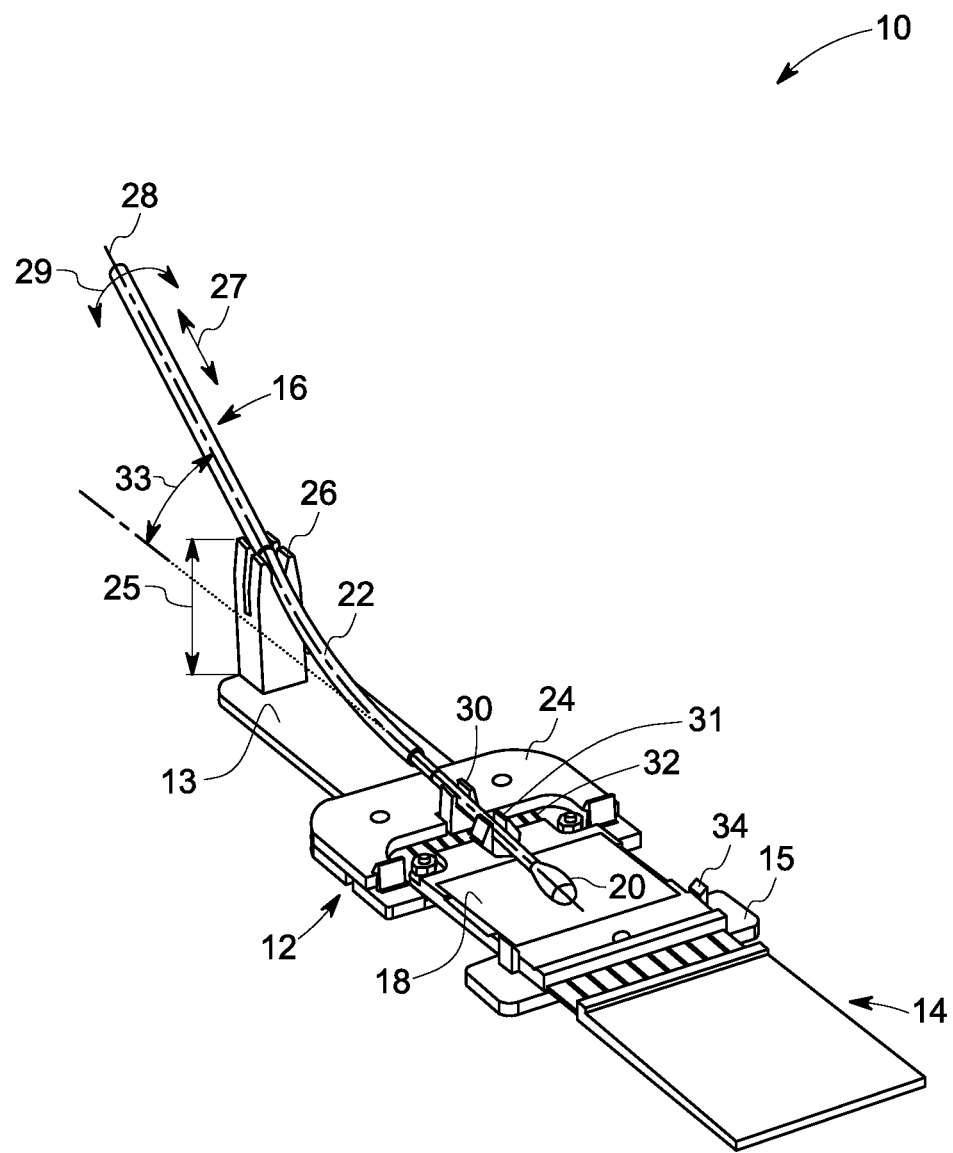
FIG. 1 is a perspective view of an example assistive sample collection and storage assembly, in accordance with aspects of the present disclosure.

FIG. 1 illustrates an example assistive sample collection and storage assembly 10. The assembly 10 may include a sample collection device 12 and a sample storage device 14. The assembly 10 may be configured to allow a trained or an untrained user to efficiently collect and store a biological sample. By way of example, the assistive sample collection and storage assembly 10 may be configured to collect a biological sample (not shown) from the user, and successfully transfer and store a desirable volume of the collected sample in a desirable location of the sample storage device 14 with repeatability.

In the illustrated embodiment, the assistive sample collection and storage assembly 10 is configured to collect the biological sample using a sample collection member 16. Further, the assembly 10 is configured to transfer the collected biological sample from the sample collection member 16 to a sample substrate 18 of the sample storage device 14. The sample substrate 18 is configured to chemically stabilize and store the biological sample for further analysis. The design of the assistive assembly 10 is configured to facilitate reproducible volume and location of the sample on the substrate 18.

In some embodiments, the sample collection device 12 may have a first portion 13 and a second portion 15 that are connected by a living hinge 32. In one embodiment, the living hinge 32 is a thin flexible hinge or a flexure. In one example, the living hinge 32 may be made from the same material as the portions 13 and 15 of the sample collection device 12. Non-limiting examples of the material for the portions 13 and 15 may include, plastic, metal, rubber, or combinations thereof. In one embodiment, a sub-portion 24 of the first portion 13 may be a separate component. In this embodiment, the sub-portion 24 may be configured to be releasably or permanently coupled to the first portion 13. The living hinge 32 may be configured to limit the relative rotational motion between the first portion 13 and second portion 15. Further, the living hinge 32 is configured to provide fatigue resistance. In one example, the living hinge 32 may be injection molded. In another example, the entire assembly 10 including the sub-components may be injection molded.

The sample collection member 16 includes a head 20 and a body 22. In one embodiment, the sample collection member 16 may be an off-the-shelf swab. In another embodiment, the sample collection member 16 may be a customized swab. Moreover. in some embodiments, the sample collection member 16 may form an integral part of the sample collection device 12. In another embodiment, the sample collection member 16 may be a physically separate entity from the sample collection device 12. In this embodiment, the sample collection member 16 may be coupled or decoupled from the sample collection device 12, as needed. By way of example, the sample collection member 16 may be coupled to the sample collection device 12 before collecting the sample. As illustrated, in some embodiments, the body 22 of the sample collection member 16 may be disposed on fastener 26. The fastener 26 may have a determined height (h), generally represented by reference numeral 25. Further, the fasteners 26 and 30 may be configured to facilitate rotation of the sample collection member 16 along a longitudinal axis of the sample collection member 16, represented generally by reference numeral 28. The fasteners 26 and 30 are configured to hold the sample collection member 16 while transferring the sample from the head 20 of the sample collection member 16 to the sample substrate 18. The fasteners 26 and 30 may be configured to permanently or releasably couple the sample collection member 16 to the device 12. The fasteners 26 and 30 are configured to provide a desirable angle 33 to the swab 16 when the head 20 of the sample collection member 16 is in contact with the sample substrate 18 for transfer of the sample. The height (h) 25 of the fastener 26 may be determined based on an angular value that is desirable for the angle 33. Additionally, the fastener 31 is configured to secure the head 20 of the sample collection member 16, thereby preventing the head 20 of the sample collection member 16 from moving along the plane of the sample substrate 18, during transfer of the sample. Non-limiting examples of the fasteners 26, 30 and 31 may include clasps, holders, ties, closures, snaps, pins, clips, toggles, or combinations thereof. The fasteners 26 and 30 may employ similar or different types of fastening means. In one embodiment, the fasteners 26, 30 and 31 may be an integral part of the sample collection device 12. The fasteners 26, 30 and 31 may be configured to limit the translational motion of the sample collection member 16, where the translational motion is generally represented by reference numeral 27. Further, the fasteners 26, 30 and 31 are configured to allow rotation of the sample collection member 16, as represented by reference numeral 29. Moreover, the fasteners 26 and 30 are configured to hold and bend the sample collection member 16 to an optimal angle 33 for applying force at the head 20 of the sample collection member 16 to facilitate transfer of the biological sample from the sample collection member 16 to the sample substrate 18.

Figure 2:
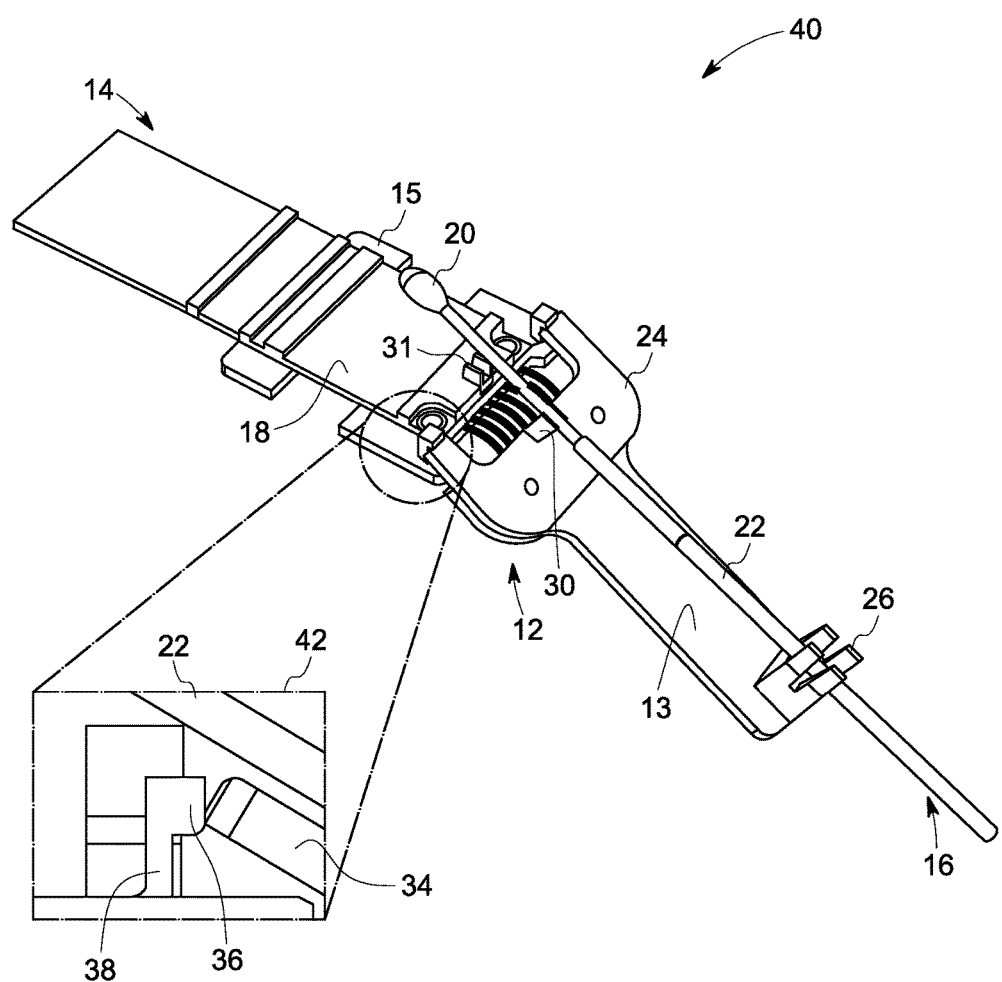
FIG. 2 is a perspective view of the example assistive sample collection and storage assembly of FIG. 1 in a first state, where a sample collection member is disposed at a distance from a sample substrate.
Figure 3:
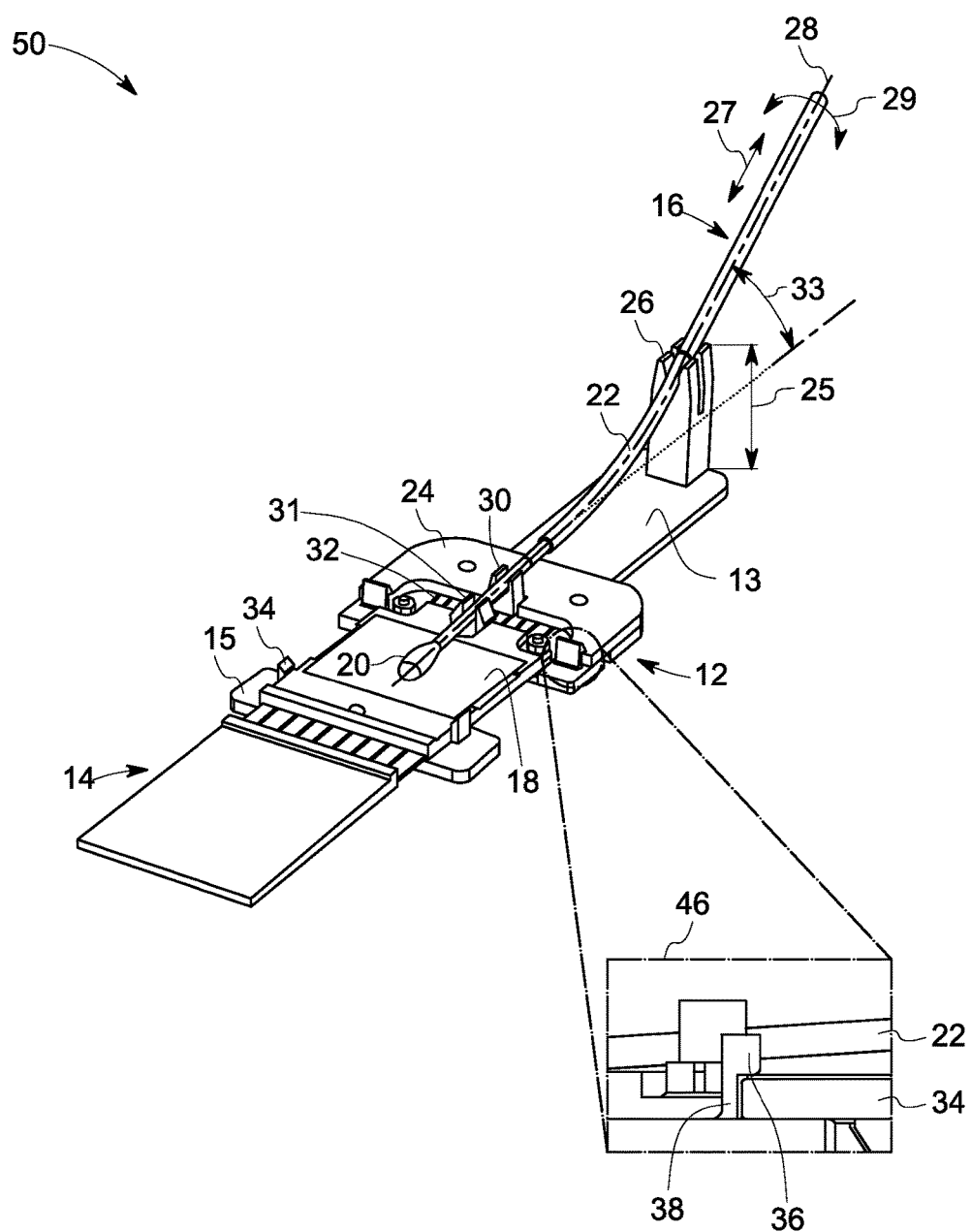
FIG. 3 is a perspective view of the example assistive sample collection and storage assembly of FIG. 1 in a second state, where at least a portion of a sample collection member is in physical contact with at least a portion of a sample substrate.

In a non-limiting example, the detent elements 34, 36 and the living hinge 32 enable a bi-state operation of the sample collection and storage assembly 10. By way of example, as illustrated in FIG. 2, the detent elements 34, 36 and the living hinge 32 enable the assembly 10 to exist in the first state by allowing the sample collection member 16 to be disposed away from the sample substrate 18. Further, as illustrated in FIG. 3, the detent elements 34, 36 and the living hinge 32 enable the assembly 10 to exist in the second state by allowing the sample collection member 16 to be in physical contact with a surface of the sample substrate 18 at a desirable angle 33 to facilitate the transfer of the sample from the sample collection member 16 to the sample substrate 18 in the second state of the assembly 10. The sample collection and storage assembly 10 is configured to switchably change between the first and second states.

FIGS. 2-3 provide detailed views of detent elements employed in the assistive sample collection device 12 which enables the bi-state operation of sample collection and storage assembly 10 of FIG. 1. FIG. 2 illustrates an embodiment 40 of the assistive assembly 10 of FIG. 1, where the sample collection device 12 and the sample storage device 14 are in the first state of the bi-state design of the assembly 10. An enlarged view of the detent mechanism is represented by reference numeral 42. In the illustrated embodiment of FIG. 2, the detent mechanism 42 of the assembly 10 enables the assembly 10 to be in the first state, where the head 20 of the sample collection member 16 is disposed away from the sample substrate 18. To maintain the first state the device 12, a detent element 34 on the sub-portion 24 of the first portion 13 is configured to interfere with a detent element 36 having a base 38. In one embodiment, the interference between the detent element 36 and 34 retains the sample collection member 16 away from the sample substrate 18. The living hinge 32 is flexed such that the detent element 36 is brought in physical contact with the detent element 34.

FIG. 3 illustrates the assembly 10 in the second state of the bi-state design of the assembly 10. In the illustrated embodiment, an example detent mechanism is illustrated by reference numeral 46. The detent mechanism 46 of the assembly 10 enables the assembly 10 to be in the second state. The detent element 36 and 34 are in a locked position to configure the sample collection member 16 to make physical contact with a surface of the sample substrate 18. In the second state, at least a portion of the sample collected by the sample collection member 16 may be transferred to the sample substrate 18. In the illustrated embodiment of FIG. 3, the second state is obtained when the detent element 34 rests below an overhanging portion of the detent element 36. The detent element 36 is configured to bend without breaking as the tab 34 is rotated towards the base 38 of the detent element 36. In one example, a user holding the first and second portions 13 and 15 of the sample collection device 12 may rotate the two portions 13 and 15 relative to one another to obtain the second state of the assembly 10. In the second state of the assembly 10, the sample collection member 16 maintains physical contact with the sample substrate 18. In one embodiment, in the second state, the sample collection member 16 may be configured to maintain physical contact with the sample substrate 18 without using any external loads or pressure.

In the illustrated embodiment, the sample collection member 16 is configured to apply a determined amount of force on the sample substrate 18 to facilitate transfer of at least a portion of the sample from the sample collection member 16 to the sample substrate 18. In the illustrated embodiment, the arrow 29 illustrates the rotational movement of the sample collection member 16 around the axis 28 to facilitate transfer of the sample from the sample collection member 16 to the sample substrate 18. In certain embodiments, an optimal bending angle 33 for the sample collection member 16 may be in a range from about 5 degrees to about 35 degrees. The heights of the fasteners 26, 30 and 31 may be selected to provide the optimal angle to the sample collection member 16 to facilitate transfer of the sample from the sample collection member 16 to the sample substrate 18.

After transfer of the sample, the devices 12 and 14 may be decoupled. In some embodiments, the devices 12 and 14 may be decoupled while the assembly 10 is still in the second state. In alternative embodiments, the devices 12 and 14 may be decoupled after switching the assembly 10 from the second state to the first state. In some of these embodiments, the head 20 of the sample collection member 16 may be positioned away from the sample substrate 18 to prevent any undesirable transfer of the sample from the sample collection member 18 to the sample substrate 18 during decoupling of the sample storage device 14 from the sample collection device 12. Further, positioning the head 20 away from the sample substrate 18 prevents any undesirable contact of the head 20 with either the sample substrate 18 or any other part of the assembly 10. In one example, the head 20 of the sample collection member 18 may be positioned away from the sample substrate 18 by the user by rotating the two portions 13 and 15 relative to one another to obtain the second state.

Figure 4:
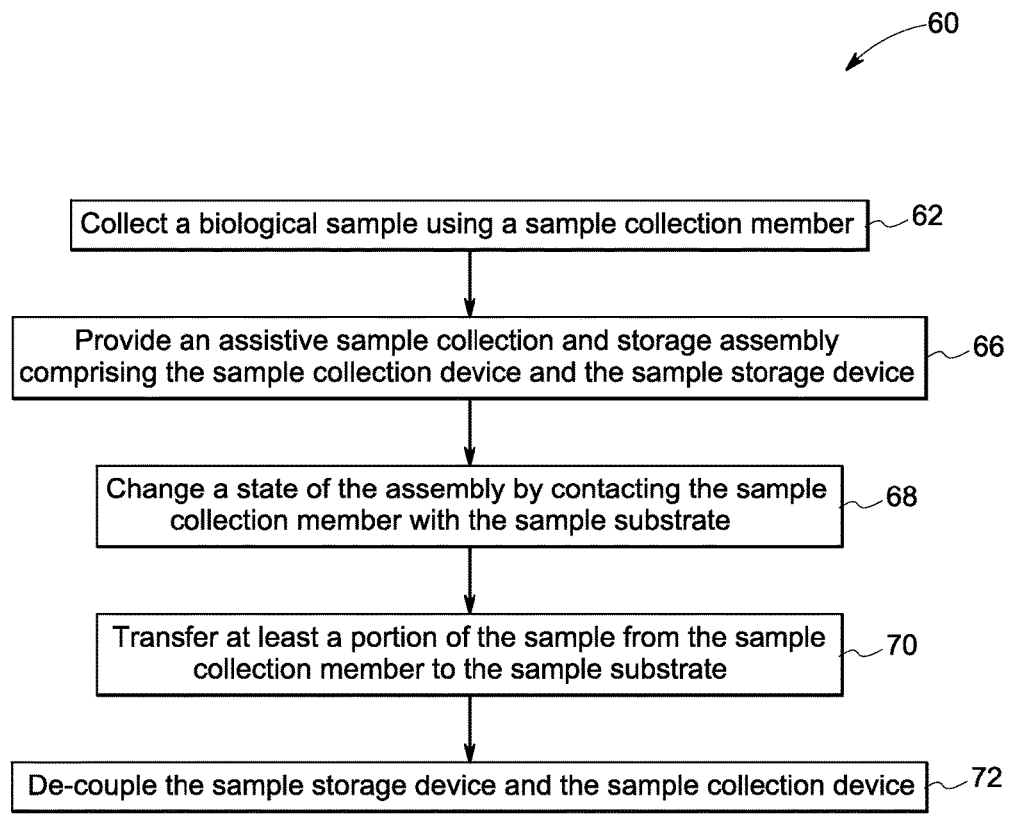
FIG. 4 is a block diagram of an example method of using an assistive sample collection and storage assembly for collecting, transferring and storing a biological sample, in accordance with aspects of the present disclosure.

FIG. 4 is an example flow chart 60 for a method for collecting, transferring and storing a biological sample using an assistive sample collection and storage assembly 10 (see FIG. 1) of the present disclosure. The method of FIG. 4 will be described with reference to assistive assembly of FIGS.

1-3 and 5-9. At block 62, the method commences by collecting a biological sample. In a non-limiting example, the sample may be collected from a patient, a criminal suspect, a victim, a scene of crime, a plant, a fungus. In one embodiment, the user of the assembly may be a trained technician, in an alternative embodiment, the user of the assembly may be a person who is not a trained technician. In one embodiment, the sample collection member may be disposed in the sample collection device while collecting the sample. In another embodiment, the sample may be collected using the sample collection member, and subsequently, the sample collection member may be coupled to the sample collection device to facilitate transfer of at least a portion of the sample from the sample collection member to the sample substrate. In one example, the sample collection member may be coupled to the sample collection device using a snap-in mechanism. However, as will be appreciated, other fastening mechanisms, such as clipping, adhesive, and the like may also be used to couple the sample collection member to the sample collection device. In one example, a user may use an off-the-shelf swab to collect the sample.

In some embodiments, the sample collection device may be available in two or more portions. In these embodiments, one of the portions of the sample collection device may be coupled to the sample collection member to collect the sample. The sample collection member may be pre-fitted in the portion. Alternatively, the sample collection member may be coupled to the portion of the sample collection time at the time of use.

In addition, at block 66, the sample collection and storage assembly is provided. The sample collection and storage assembly may be provided in a first state. In some embodiments, the step of providing the assistive sample collection and storage assembly includes coupling the sample collection member to the sample collection device after collecting the sample. In these embodiments, the sample collection device and the sample storage devices may be already coupled to each other at the time of sample collection.

In other embodiments, the step of providing the assistive sample collection and storage assembly includes releasably coupling the sample collection device having the sample collection member to the sample storage device. In these embodiments, the sample collection member may be already coupled to the sample collection device at the time of sample collection.

It should be noted that in embodiments where the assistive sample collection and storage assembly has a monolithic structure, the step of providing the assembly may be redundant.

Furthermore, at block 68, the state of the assistive sample collection and storage assembly may be switched from the first state to a second state to provide physical contact between the sample collection member and the sample substrate. The fasteners may be used to prevent undesirable movements of the sample collection member in the second state of the assembly. In particular, fasteners may be used to prevent undesirable movements of the sample collection member during transfer of the sample from the sample collection member to the sample substrate.

At block 70, at least a portion of the sample is transferred from the sample collection member to the sample substrate. In one embodiment, the sample may be transferred by applying force on the sample collection member such that the head of the sample collection member is pressed against the sample substrate, and at least a portion of the sample is transferred to the sample substrate. In one embodiment, the head of the sample collection member may be rotated along a longitudinal axis of the sample collection member one or more times to ensure that sample is transferred from the surface area of the head of the sample collection member. The sample from the head of the sample collection member may be transferred to the substrate by applying a force on the head of the sample collection member.

Moreover, at block 72, subsequent to the transfer of the sample, the sample collection device is decoupled from the sample storage device. It should be noted that optionally, after transfer of the sample, but prior to decoupling of the sample collection and sample storage devices, the sample collection device may be returned to the first state prior to decoupling the devices. In certain embodiments, the assistive sample collection and storage assembly may be made using one or more of rapid prototyping, molding, casting, injection molding, machining, or combinations thereof.

Figure 5:
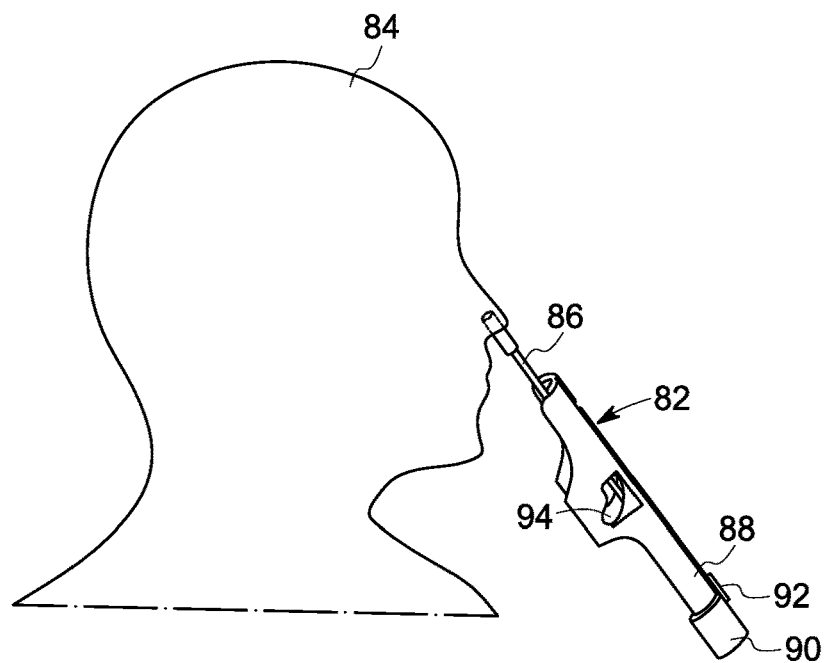
FIG. 5 is a perspective view of a first portion of a sample collection device in use, in accordance with aspects of the present disclosure.

FIG. 5 illustrates an example embodiment 80 of a portion of an assistive sample collection and storage assembly, such as the assistive assembly of FIG. 1, being used by a user 84 to collect a nasal sample. In the illustrated embodiment, the user 84 employs a first portion 82 of a sample collection device (not shown) to collect the sample. In the illustrated embodiment, the first portion 82 of the sample collection device is configured to receive a sample collection member 86 (e.g., a nasal swab). In the illustrated embodiment, the sample collection member 86 is embedded in a body 88 of the first portion 82. In one embodiment, the sample collection member 86 may be coupled to the first portion 82 at the time of use, e.g., before and during collecting the sample. In another embodiment, the sample collection member 86 may be coupled to the first portion 82 of the sample collection device after collection of the sample. The sample collection member 86 may be configured to be snapped into the first portion 82. Moreover, in one embodiment, the sample collection member 86 may be an off-the-shelf swab.

In the illustrated embodiment, the sample collection member 86 includes a handle 90. The handle 90 of the sample collection member 86 provides the provision for holding the sample collection device. By way of example, at the time of sample collection, the user 84 may hold the sample collection member 86 using the handle 90. The sample collection member 86 may be rotated using the handle 90. As will be appreciated, rotation of the sample collection member 86 facilitates sample collection.

Figure 6:
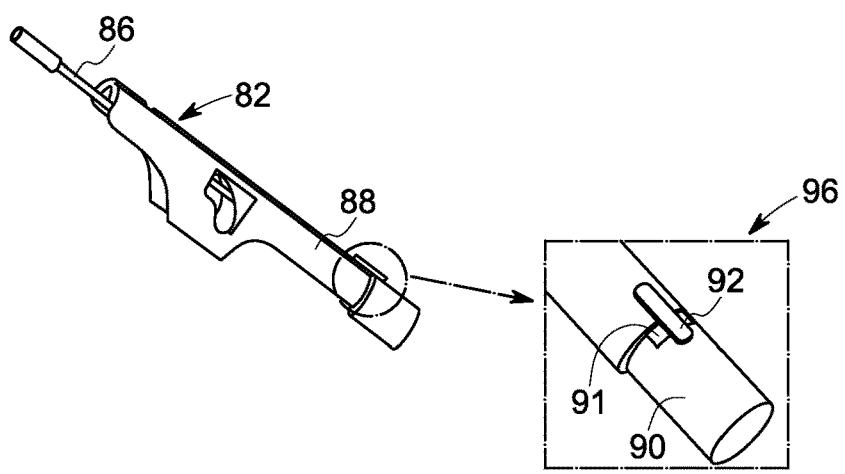
FIG. 6 is a perspective view of the first portion of the sample device of FIG. 5.

FIG. 6 illustrates the first portion 82 of the sample collection device (not shown) and the sample collection member 86. The body 88 and handle 90 of the sample collection member 86 include detent elements 91 and 92 to track number of rotations of the sample collection member 86. An enlarged view 96 shows detent elements 91 and 92. Additionally, the body 88 of the first portion 82 includes a second detent element 94 configured to achieve a bi-state design of the assembly.

The detent elements 91 and 92 provide a feedback to the user regarding the number of rotations of the sample collection member 86 that have been completed during collection or transfer of the sample. The feedback may be provided by using mechanical means to produce a tactile sensation, where the detent haptic feedback is provided at the completion of a rotation. In one example, the feedback from the detent elements 91 and 92, may be provided using an audible clicking sound from the detent elements 91 and 92, where the clicking sound is provided at the completion of a rotation. In one embodiment, controlling the number of rotations helps to improve reproducibility of the sample transfer. Further, the detent elements 91 and 92 also help prevent the user from rotating less than one complete rotation, in which case some portion of the sample collection member 86 may not come in physical contact with the sample substrate (not shown). Further, the detent elements 91 and 92 may be provided in the first portion 82 to prevent the sample collection member 86 from undesirably rotating while collecting the sample (e.g., mucus sample).

As illustrated in FIG. 6, the assembly may include elements that enhance ergonomics and user-friendliness of the assembly. In particular, the first portion 82 may be designed to provide the user with an ergonomically suitable grip. By way of example, a size of element 90 of the sample collection member may be suitable for the user to hold element 90 with the hand and rotate element 90 during sample collection or transfer.

Figure 7:
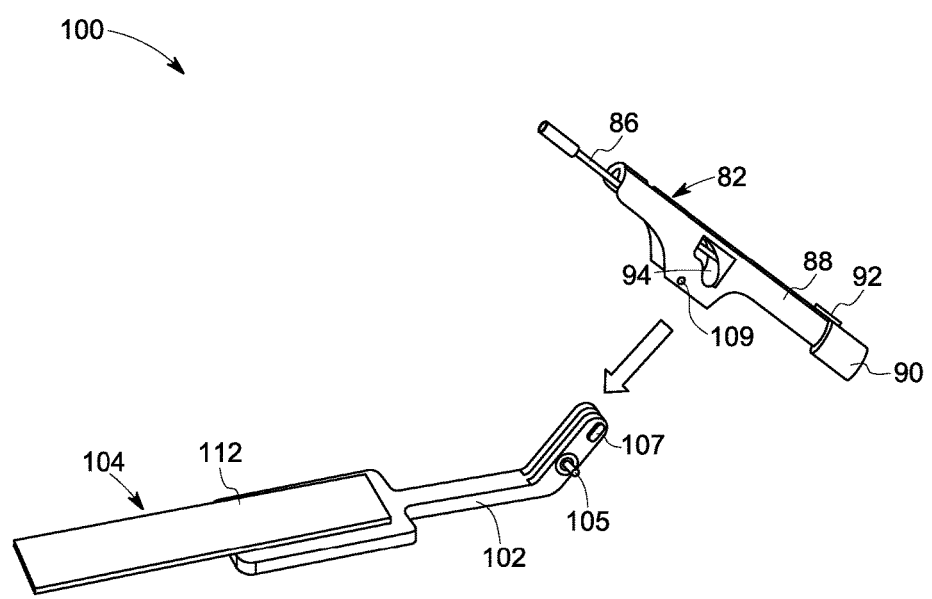
FIG. 7 is an exploded view of an assistive sample collection and storage assembly, in accordance with aspects of the present disclosure.

FIG. 7 illustrates an exploded view 100 of an assistive sample collection and storage assembly employing the sample collection member 86 (see FIG. 5) and first portion 82 of the sample collection device. In operation, subsequent to the collection of the sample by the first portion 82 of the sample collection device, the first portion 82 may be coupled to a second portion 102 of the sample collection device to form a sample collection device. Further, a sample storage device 104 may be coupled to the second portion 102 of the sample collection device to form the assistive sample collection and storage assembly. The sample collection device having the portions 82 and 102 may include one or more fasteners configured to couple the sample storage device 104 to the sample collection device. The fasteners may be configured to allow the assembly to switch between the first and second states. In one embodiment, the first portion 82 may include a counterpart of the fasteners to facilitate coupling of the first portion 82 of the sample collection device to the second portion 102 of the sample collection device. Further, the second portion 102 of the sample collection device may include a detent element 107 corresponding to detent element 94.

Detent elements 94 and 107 having a double-detent design is configured to achieve a bi-state design wherein the assembly is able to keep the sample collection member 86 away from the sample substrate until the user snaps the device to bend the sample collection member 84 at the optimal angle against the sample substrate. The detent element 107 may be moved within the detent element 94 to enable the switch between the first and second states of the assembly. Also, fasteners 105 and 109 may be used to couple the portions 82 and 102 of the sample collection device.

Figure 8:
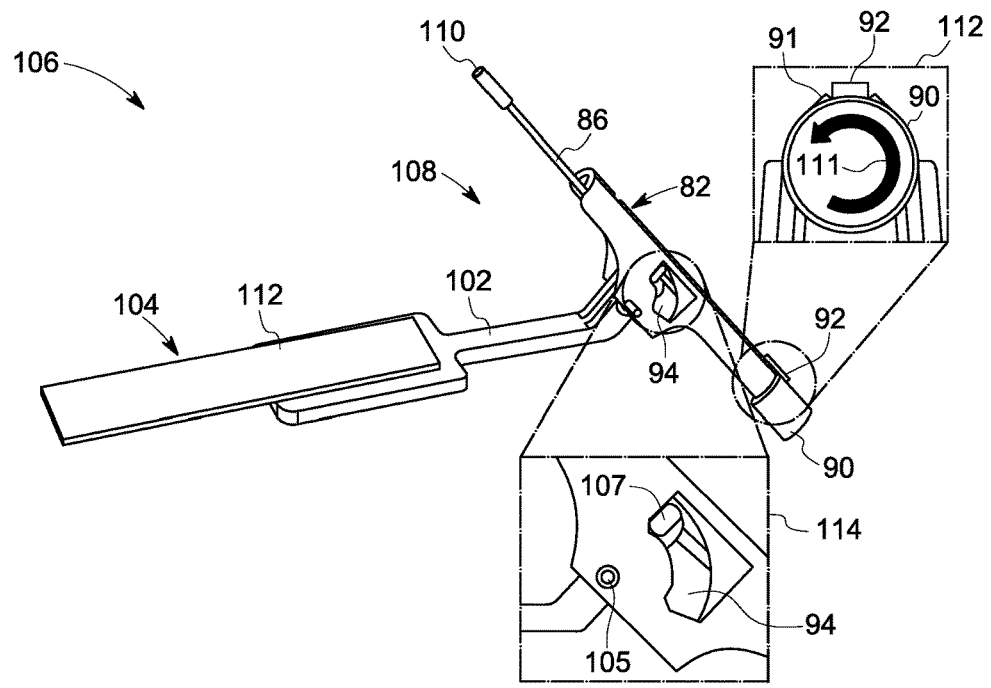
FIG. 8 is a perspective view of the assistive sample collection and storage assembly of FIG. 7 in a first state.

FIG. 8 illustrates a first state of an assistive sample collection and storage assembly 106 or a sample collection device 108. The assembly 106 includes the sample collection device 108 and the sample storage device 104. In the first state, the portions 82 and 102 of the sample collection device 108 are disposed such that a head 110 of the sample collection member 86 is disposed at a distance from a sample substrate 112 of the sample storage device 104.

The assistive sample collection and storage assembly 106 is configured to exist in two discrete states that can be transitioned to one another by rotating the first portion 82 relative to the second portion 102 or the sample storage device 104. In the first state, the portions 82 and 102 of the sample collection device 108 are disposed such that the head 110 of the sample collection member 86 is disposed at a distance from a sample substrate 112 of the sample storage device 104.

Reference numeral 113 represents an enlarged view of the detent elements 91 and 92. As illustrated in the enlarged view 113, the handle 90 of the sample collection member 86 includes detent element 91 and is configured to rotate as generally represented by reference numeral 111. An enlarged view of detent elements 94 and 107 in the first state of the assistive sample collection and storage assembly 106 is represented generally by reference numeral 114.

Figure 9:
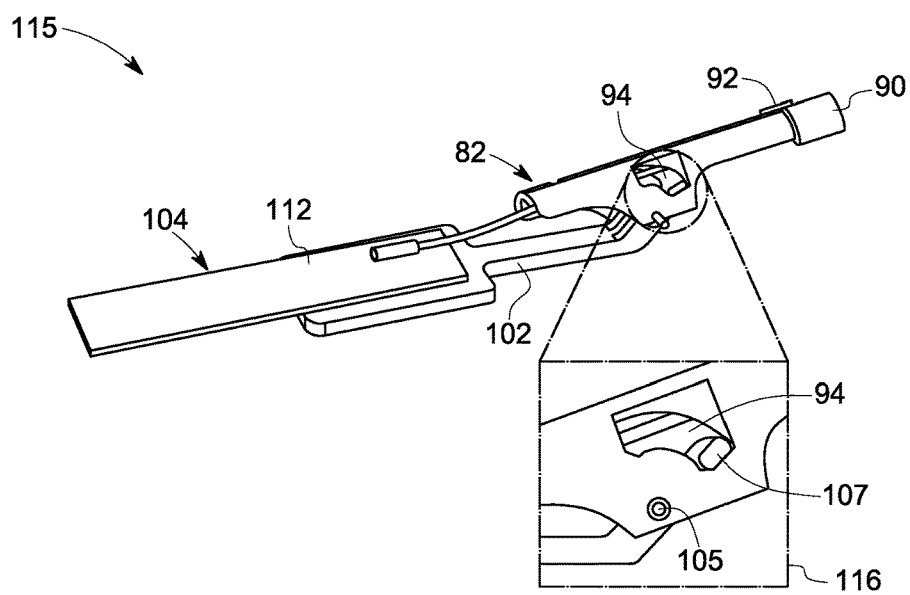
FIG. 9 is a perspective view of the assistive sample collection and storage assembly of FIGS. 7-8 in a second state.

FIG. 9 depicts an embodiment 115 of the assistive sample collection and storage assembly. As illustrated in FIG. 9, in the second state, the portions 82 and 102 of the sample collection device 108 are disposed such that at least a portion of the head 110 of the sample collection member 86 is in direct physical contact with a portion of a surface of the sample substrate 112 of the sample storage device 104. In the second state, the sample collection member 86 is bent at an optimal angle with respect to the second portion 102 or the sample storage device 104 to maintain an optimal contact force between the head 110 of the sample collection member 86 and the sample substrate 112 on the sample storage device 104. By rotating the sample collection member 86 using element 90 of the sample collection member 86, at least a portion of the biological sample is transferred to the sample substrate 112 of the sample storage device 104. The sample may be transferred with reproducible location, percentage of transferred sample and sample concentration (volume per unit area). This transfer method is compatible with different types of collection members (e.g., swab) with an axially-symmetric head that can collect a sample by rotation and a relatively flexible body. The device is designed to be easy to use and mistake-proof.

An enlarged view of the detent elements 94 and 107 in the second state of the assistive sample collection and storage assembly 106 is represented generally by reference numeral 116. As illustrated, in the second state, the head 110 of the sample collection member 86 is in physical contact with the sample substrate 112. The detent elements 94 and 107 having a double-detent design is configured to achieve a bi-state design. In particular, the detent element 107 disposed within the detent element 94 is able to switch between a first position as illustrated in the enlarged view 114 (FIG. 8), and the second position as illustrated in the enlarged view 116. The shifting of the position of the detent element 107 occurs when a user snaps the first portion 82 to bend the sample collection member 86 at the optimal angle to the sample substrate 112.

In one embodiment, subsequent to the transfer of the sample, the detent elements 94 and 107 are configured in the first state, and the sample collection device 108 is decoupled from the sample storage device 104. In another embodiment, subsequent to the transfer of the sample, the detent element may be maintained in the second state, and the sample collection device 108 is decoupled from the sample storage device 104.

In certain embodiments, the assembly utilizes the flexibility of the sample collection member to create desirable consistent contact force by bending/flexing the sample collection member at an optimal angle against the surface of the sample substrate. Further, one or more elements of the sample collection device may be configured to guide the head of the sample collection member and ensure that the head of the sample collection member stays in the same desirable position during a sample transfer. In addition to features and elements described herein above, the assistive sample collection and storage assembly may also include one or more elements to prevent user mistakes, for example, a guide that stops undesirable rotation of the sample collection member. The guide may be configured to prevent the handle which includes the sample collection member from rotating about the base, before the handle snaps onto the base. This snapping of the handle in the base prevents premature contact between the sample collection member and the sample substrate. With all these elements, the assistive sample collection and transfer assembly becomes easier to use and mistake-proof. The assembly may also include a cover that prevents undesirable finger contact with the substrate and so forth. The assistive sample collection and transfer assembly facilitates reproducible biological sample transfer in both location and percentage of transferred volume from an off-the-shelf or customized swab to the sample substrate by a trained or novice user using the assembly, while making the assembly mistake-proof.

Example 1

In one example, an arrangement 130 of an experimental set-up is provided to determine an optimal bending angle for a sample collection member, such as a swab. As illustrated in FIGS. 10(a)-10(b), the arrangement 130 includes a peg board 140. A swab 142 is coupled to the peg board 140 using c-clips 144 and 146. The number and positions of the clips 144 and 146 may be varied on the peg board 140 to obtain different bending angles 148 and 154 of the swab 142 to facilitate contact between the swab 142 and the sample substrate 150. Patterns 152 and 156 represent positions of the transferred sample on the sample substrate 150. The pattern 152 corresponds to the position of the swab 142 as illustrated in FIG. 10(a). Similarly, the pattern 156 corresponds to the position of the swab 142 as illustrated in FIG. 10(b).

Sample transfer efficiency is analyzed quantitatively to determine the optimal bending angle. The transfer efficiency is quantified by a volume of sample in a 3 mm diameter sample area (the current sample isolation area). Amount of sample transferred from the swab 142 on the sample substrate 150 is obtained by measuring a weight change of the sample substrate 150 before and after transfer of the sample. The optimal number of turns of the swab required to transfer a desirable amount of the sample is also determined with this arrangement by evaluating the transfer efficiency and substrate damage.

The experimental procedure included disposing the swab in place and aligning the head of the swab at a desirable location on the substrate. In the illustrated embodiment of FIG. 11, the head of the swab is aligned with a hole on the peg board. Next, retaining rings are installed to prevent front and back movement of the swab. The weight of the swab and the substrate are measured. Furthermore, about 50 µL of mucus sample is applied on an interior of a pipette using a syringe. The swab is rolled against the interior of the pipette to transfer the sample on the swab. The swab with the mucus sample is weighed. Subsequently, the swab is disposed on the peg board. In addition, a suitable surface (e.g., a paper) is disposed on the substrate. Next, the peg board and the substrate are arranged such that there is physical contact between the swab head and the substrate. While in contact with the substrate, the swab is rotated ten times to facilitate transfer of the mucus sample from the swab head to the substrate. Subsequent to the transfer of the sample, the swab and the substrate paper are released and weighed. FIG. 11 illustrates images of examples of the transferred samples and the corresponding swab angles.

The transfer efficiency is quantified by the volume of mucus in a 3 mm circle, which equals the amount of mucus that DNA/RNA can be eluted from in the work flow. This can be obtained by measuring the weight change of the substrate before and after and the computing the mucus spot size using image processing. The results are listed in Table 1. It is observed that for a bending angle larger than the bending angle 148 of FIG. 10(a), the transferred volume in a 3 mm² area does not increase as bending angle increases.

TABLE 1

| | S. No. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Angle (degrees) | 0 | 4.7 | 9.5 | 14 | 18.4 | 22.6 | 26.6 | 5.8 | 10.5 | 15 | 19.1 | 21.5 | 24.2 | 26.8 |
| Vol. per 3 mm² (µL) | 1.08 | 1.63 | 1.84 | 1.75 | 1.90 | 1.72 | 1.73 | 1.52 | 1.61 | 1.48 | 1.71 | 1.63 | 1.64 | 1.67 |

An amount of food dye that is less than about 10 µL in 1.5 mL mucus sample is used. A ETF31 base paper is used as a surface of the substrate. About 50 µL of mucus sample is used for each position of the bending angle of the swab. Further, two different locations for the front c-clip (close to the swab head) and seven locations for the rear c-clip are evaluated. The swab is rotated for ten turns to transfer the sample from the swab to the substrate.

Initially, the swab is disposed parallel to a surface of the substrate, the bending angle of the swab at this stage may be considered to be zero degrees. For bending angles of the swab above zero degrees, the transferred volume in a 3 mm diameter area does not increase immediately with the increase in the bending angle in. However, bending angles greater than about 22.6 degrees (e.g., config. 6) may cause excessive force on the surface of the substrate, thereby damaging the substrate. Considering an amount of the transferred volume of the sample and substrate damage, an optimal bending angle in a range from about 5 degrees to about 10 degrees is determined. An average volume of the sample transferred from the swab to the substrate in a 3 mm elution area is about 1.67 µL±0.21 µL. A position of the transferred sample on the substrate is analyzed using image processing. A center position of the transferred sample relative to the peg board has deviation of up to about 0.8 mm in both horizontal and vertical directions (represented by x- and y-axes, respectively). The arrangement demonstrated reproducibility in the volume of the sample transferred and location of the sample on the substrate.

Example 2

A volume of the biological sample transferred from the substrate was obtained by measuring a weight of the substrate before and after the transfer of the biological sample.

The position of the transferred mucus spot was analyzed using image processing in Matlab. A schematic of an overlapped image 160 of all transferred samples 162 is shown in FIG. 11. A darker area 164 indicates the common area shared by all the mucus samples. The darker area 164 covers the interior 3 mm² compression seal 166, which is shown as the circle. One can wrap a rectangle around the sample with the edges parallel to the image edges. The center position of such rectangle referenced to the corner of the peg board is obtained for each sample. The results are shown in Table 2. Mucus spot positions after transfer. The center position has small standard deviation of 0.8 mm in both horizontal and vertical direction.

In the illustrated embodiment of FIG. 11, the transferred sample images are added together. The rings 164 indicate the compression seal. The region 166 indicates a common area shared by all samples.

Advantageously, the assembly is lightweight and compact in size. In one example, the assembly may weigh in a range from about 15 grams to about 50 grams. Further, the assembly is injection moldable, without need for any further processing. Hence, the assembly may be manufactured at a low cost. Moreover, the customized swab may also be manufactured in a cost-effective fashion. In some embodiments, the device may be used in a multi-analyte point-of-care diagnostic platform that encompasses the entire sample collection to sample analysis workflow. The assembly enables a method to transfer biological sample from a swab to substrate paper by bending a swab. Such a method of sample transfer is compatible with a variety of swabs and is applicable to a wide range of biological samples. Further, the assembly is easy-to-use and mistake proof. Accordingly, the assembly may be used by users including untrained persons in clinical or non-clinical settings.

While only certain elements of the invention have been illustrated and described herein, many modifications and changes will occur to those skilled in the art. It is, therefore, to be understood that the appended claims are intended to cover all such modifications and changes as fall within the scope of the invention.

The invention claimed is:

1. An assistive sample collection and storage assembly for collecting, transferring, and storing a biological sample, comprising:
a sample collection device comprising a first portion and a second portion, wherein the first portion of the sample collection device is configured to receive a sample collection member, and wherein the sample collection device and sample collection member comprise detent elements to determine a number of rotations of the sample collection member;
a sample storage device comprising a sample substrate, wherein the sample substrate is configured to receive at least a portion of the biological sample from the sample collection member,
wherein the assistive sample collection and storage assembly is configured to exist in a first state and a second state, wherein the sample collection member is disposed at a determined distance from the sample substrate in the first state, wherein at least a portion of the sample collection member is in physical contact with at least a portion of the sample substrate in the second state, and wherein the sample collection member is configured to apply a determined amount of force between the sample collection member and the sample substrate in the second state of the assembly.

2. The assistive sample collection and storage assembly of claim 1, wherein the sample collection device and the sample storage device are configured to be releasably coupled to each other.

3. The assistive sample collection and storage assembly of claim 1, wherein the sample collection member is a customized swab or an off-the-shelf swab.

4. The assistive sample collection and storage assembly of claim 1, wherein the first and second portions of the sample collection device are releasably coupled to each other.

5. The assistive sample collection and storage assembly of claim 1, wherein the sample collection member comprises a handle configured to rotate the sample collection member.

6. The assistive sample collection and storage assembly of claim 1, wherein the second portion of the sample collection device is configured to receive a sample storage device.

7. The assistive sample collection and storage assembly 1, wherein the sample collection member is configured to rotate about a longitudinal axis of the sample collection member while being disposed in the first portion of the sample collection device.

8. The assistive sample collection and storage assembly of claim 1, further comprising a living hinge configured to define a relative motion between the first and second portions of the sample collection device.

9. The assistive sample collection and storage assembly of claim 1, wherein the sample collection and storage assembly is configured to switchably change from the first state to the second state, and vice versa.

10. The assistive sample collection and storage assembly of claim 9, further comprising a detent element configured to lock the portions of the sample collection device in the first state, the second state, or both.

11. The assistive sample collection and storage assembly of claim 1, wherein a surface of the sample collection member comprises a flocked surface.

12. The sample collection and storage assembly of claim 1, wherein the sample collection device further comprises fasteners configured to at least partially prevent movement of the sample collection member along a longitudinal axis of the sample collection member.

13. The assistive sample collection and storage assembly of claim 1, wherein the sample collection device is a disposable device.

14. An assistive sample collection and storage assembly for collecting, transferring, and storing a biological sample, comprising:
a sample storage device configured to store at least a portion of the biological sample;
a sample collection device comprising:
a first portion comprising:
a sample collection member having a handle configured to rotate the sample collection member;
fasteners configured to hold and bend the sample collection member against a surface of a sample substrate to apply a force at a head of the sample collection member to transfer the biological sample from the sample collection member to the sample substrate;
a second portion configured to be coupled to the first portion and the sample storage device.

15. The assistive sample collection and storage assembly of claim 14, wherein the first portion of the sample collection device further comprises detent elements configured to determine a number of rotations of the sample collection member.

16. The assistive sample collection and storage assembly of claim 14, wherein the second portion of the sample collection device further comprises a detent element configured to lock the sample collection device and the sample storage device in a first state, a second state, or both.

* * * * *